United States Patent [19]

Freeman

[11] 4,038,555

[45] July 26, 1977

[54] PHOTOMETRIC MEASURING SYSTEM

[75] Inventor: Gary M. Freeman, Houston, Tex.

[73] Assignee: Gilford Instrument Laboratories, Inc., Oberlin, Ohio

[21] Appl. No.: 501,272

[22] Filed: Aug. 28, 1974

[51] Int. Cl.² .......................................... G01N 21/24
[52] U.S. Cl. ..................... 250/573; 250/211 J; 250/214 L; 250/238; 250/564; 356/201
[58] Field of Search ............... 250/573, 206, 214, 238, 250/239, 211 J, 212, 226, 564; 356/201, 202, 226, 228, 234

[56] References Cited

U.S. PATENT DOCUMENTS

| | | | |
|---|---|---|---|
| 3,045,125 | 7/1962 | Mason | 250/238 |
| 3,463,927 | 8/1969 | Allington | 250/211 |
| 3,565,535 | 2/1971 | Monell | 356/201 |
| 3,625,621 | 12/1971 | Fields | 356/201 X |
| 3,753,388 | 8/1973 | Toyada | 356/226 X |
| 3,868,186 | 2/1975 | Paukert et al. | 250/573 X |
| 3,905,769 | 9/1975 | Carroll et al. | 250/212 X |

Primary Examiner—Eugene R. La Roche
Attorney, Agent, or Firm—Baldwin, Egan, Walling & Fetzer

[57] ABSTRACT

This invention has particular utility in the field of absorption spectrophotometry or colorimetry, and is particularly applicable, when incorporated in such type of equipment, as a sample detector to enable direct readings to be taken in concentration or absorbance of sample fluids or the like.

3 Claims, 6 Drawing Figures

PHOTOMETRIC MEASURING SYSTEM

SUMMARY

A relatively simple photodetector circuit for use with absorption spectrophotometers or like equipment for sensing light absorbance of a fluid sample and which circuit is operable to yield a logarithmic response to changes in light intensity and hence characteristic of the absorbance of said sample within a substantially wide range of radiant power, thus making it possible to provide a direct reading of concentrate of said sample, which response is substantially linear throughout said range.

The present photometric detector system includes a silicon photodiode which is connected to the input of a conventional operational amplifier and positioned to intercept the light from a test sample that is exposed to a monochromatic source of light. As is well known, silicon photodiodes possess many of the properties and/or parameters of conventional silicon diodes, but most importantly for application in the present inventive concept, the photodiode inherently possesses the property or parameter of having the open circuit voltage developed across its anode-cathode junction vary logarithmically with the change in light intensity to which the diode is exposed. In particular, in silicon photodiodes having relatively small active target areas, as for example 0.040 inches$^2$, this voltage change is observed to be approximately ±.060 volts per one unit of change in magnitude of light intensity. In actual practice this relationship has been observed to be substantially constant within a voltage range of approximately 0.050 volts to 0.400 volts absolute, and for a light intensity change of over 5 orders of magnitude. Operational amplifiers having an input impedance in excess of $10^{11}$ ohms and an input bias current less than $10^{-11}$ amperes and connected in the voltage follower configuration is preferably utilized in the present system.

The photodiode is also temperature sensitive, and it has been found that for each 15° C rise in temperature above 25° C the sensitivity of the photodiode to light decreases one order of magnitude (approximately 0.060 volts). To assure maximum stability for the instant photometric detector system throughout its operational range, a temperature controller is provided for the photodiode to retain said photodiode at an optimum operating temperature of 25° centigrade.

The photodiode voltage which is a function of the light intensity concentration or absorbance of the test sample is suitably amplified by the operational amplifier, which amplification may be accomplished in one or more distinct stages, and the resultant amplified signal output is then connected to a suitable readout instrument which produces a direct reading of optical density or concentration of the test sample. This photometric detector system is of relatively low cost suitable for inexpensive instrument investment and is adequately operational over a useful wavelength range of approximately 380 to 1100 millimicrons or nanon.

SHORT DESCRIPTION OF THE DRAWINGS

FIGS. 1 and 4A combined are a schematic wiring diagram of a preferred embodiment of the photometric measurement system of the present invention;

Figure 4A:
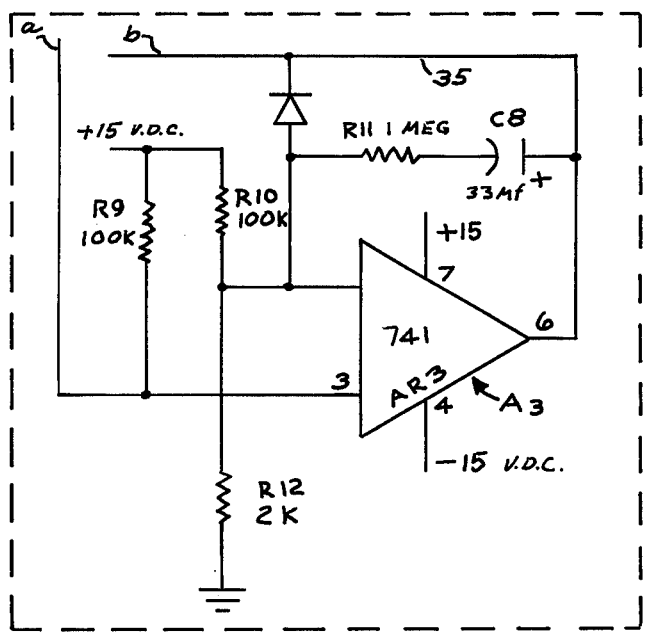
FIG. 4A is the schematic wiring diagram of the photodiode temperature controller of the measurement system.
Figure 4B:
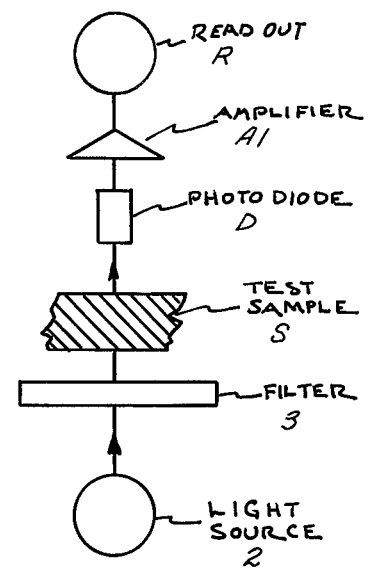
Figure 4C:
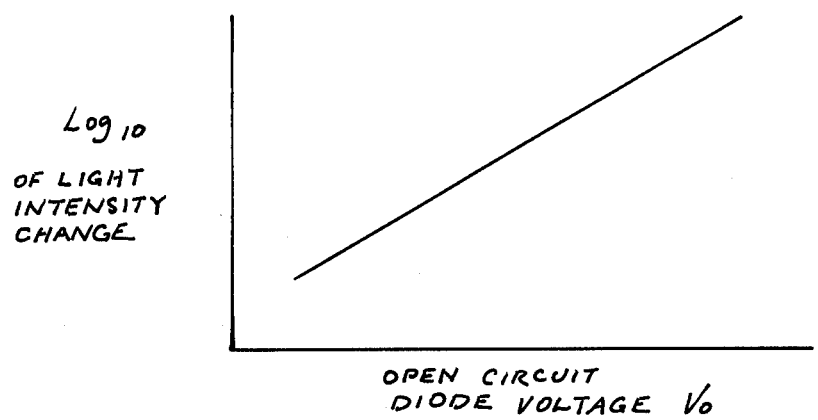

FIG. 4B is a schematic illustration of a typical spectrophotometer instrument with which the photometric measurement system of the present invention is particularly applicable; and FIG. 4C is a graph of the operational characteristics of the photodiode used in the present system, specifically the open circuit voltage $V_0$ plotted against the log of intensity change of the light to which it is exposed.

DESCRIPTION OF THE PREFERRED EMBODIMENT

With reference to the schematic diagram of FIG. 4B there is shown a typical spectrophotometer which includes a suitable monochromatic light source 2, a filter 3 interposed between the light source 2 and the position therein occupied by the sample S under test.

The light emitted by source 2 is filtered by filter element 3 and projected onto the sample S which may be, as will be understood, a material under test dissolved within a suitable reagent and which mixture is disposed within a container or the like and wherein it is desired to determine the concentrate of said material.

The intensity of the light transmitted through the sample (transmittance) inherently relates logarithmically to the concentration and absorptivity of the sample material. The transmitted light is projected onto the photodiode D which is responsive to provide an open-circuit voltage across its anode-cathode junction, the magnitude of which is a logarithmic function of the intensity of said light or is a linear function of the absorbance or concentration of the sample material.

This voltage signal from the photodiode D is connected to a conventional operational amplifier A, which may be formed of one or more distinct amplifiers wherein said signal is amplified sufficiently to drive a suitable readout instrument R and provide a direct reading in concentration or absorbance of the sample S under test.

Figure 1:
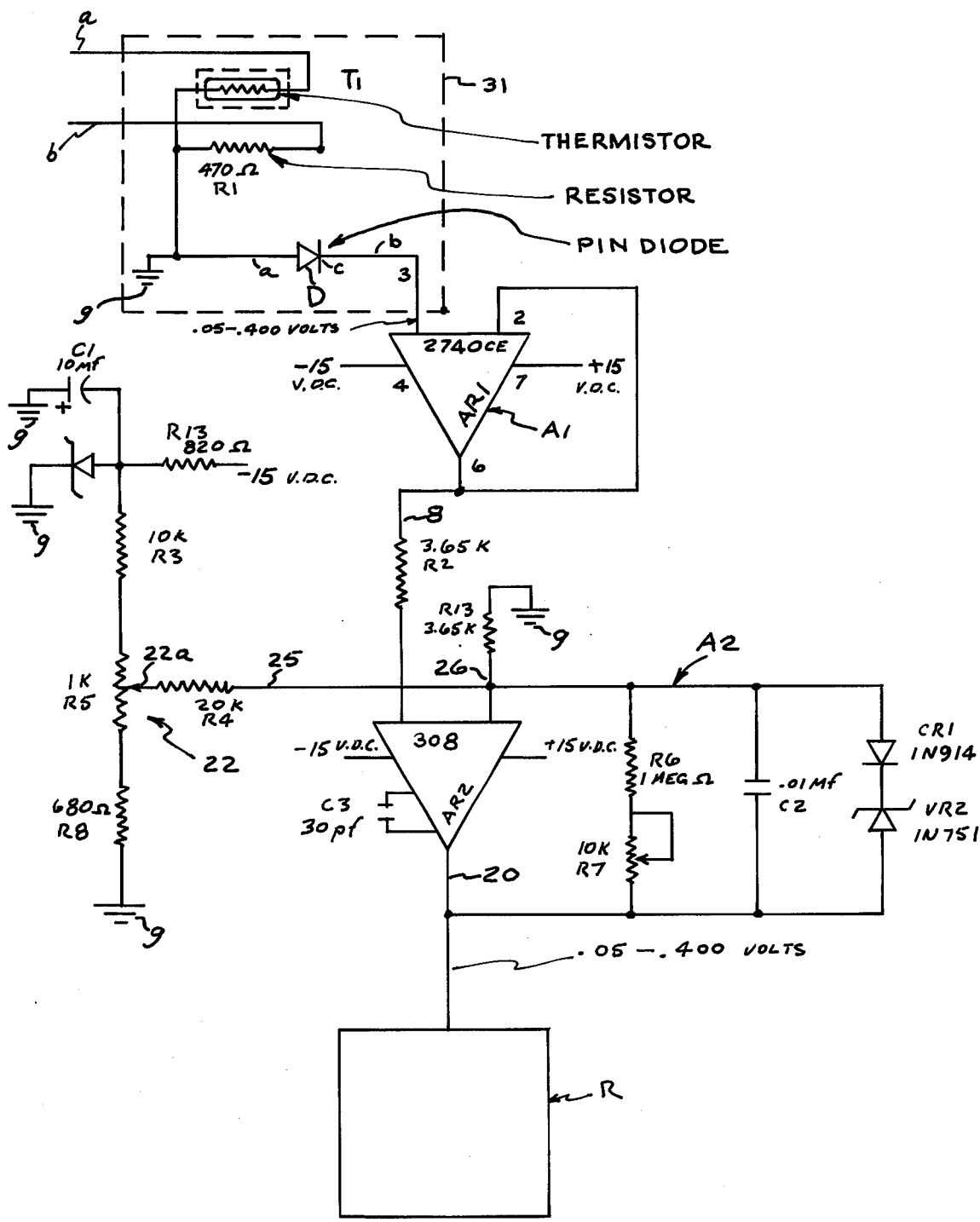

Referring now to the schematic wiring diagram of FIG. 1, a preferred embodiment of photometric measurement system of the present invention is illustrated and includes the photodiode D which, as aforesaid, is positioned in the system to intercept the light from the sample under test S and to provide an open-circuit voltage signal across its anode-cathode junction that is representative of the concentration or absorbance of the material of said sample. As seen, the cathode C of the photodiode D is connected by conductor b to the input of conventional amplifier $A_1$.

The anode of said photodiode D is connected to the instrument ground g.

The output of amplifier $A_1$ is connected through conductor 8 to the input of a second operational amplifier $A_2$, the two stages of amplification $A_1$ and $A_2$ being adequate in the present embodiment to provide a signal output sufficient to drive a conventional readout instrument which, as aforesaid, may be calibrated in units of concentration or absorbance of the material in the test sample S.

The operational amplifiers $A_1$ and $A_2$ are A.C. feedback-type amplifiers and may be of any conventional design to provide suitable amplification of the input voltage signal from the photodiode D.

The illustrated values of the circuit components associated with each of said amplifiers $A_1$ and $A_2$, and the magnitudes of the voltage sources used therewith are intended to enable said amplifiers $A_1$ and $A_2$ to function in such manner as to provide a signal output from amplifier $A_2$ (conductor 20) that its rate of change with respect to a like change in the intensity of light projected onto the photodiode is substantially linear throughout the range of operation of the system. As previously mentioned, in actual practice this voltage change is approximately ±.060 volts per one unit of change in magnitude of light intensity within a voltage range of approximately 0.050 volts to 0.400 volts absolute, and for a light intensity change of over 5 orders of magnitude. The chart of FIG. 4C graphically illustrates this operational characteristic.

The instant measurement system is capable of being calibrated using a suitable standard or calibration sample, as for example, a sample $S_c$ which contains only the reagent to be used as the carrier whereby the system may be adjusted to a zero or calibration level. Thereafter, the transmittance or absorbance of any sample mixture containing the material under test in the carrier reagent may be analyzed and compared against the calibration level.

For this purpose, the amplifier $A_2$ is provided with a zero adjustment as indicated by the potentiometer at 22.

As seen in FIG. 1, the wiper arm 22a of potentiometer 22 is connected by conductor 25 to input junction 26 of the feedback circuit of amplifier $A_2$. The potentiometer 22 is connected in circuit as shown, between the instrument ground g and a negative source of potential (−15 volts). With this circuitry, and with the calibration sample $S_c$ in the test position FIG. 4B), the wiper arm 22a may be adjusted until the output voltage signal of amplifier $A_2$ is of preselected calibrated level such as zero units as indicated on the readout instrument R.

Thereafter, with this calibrated output level of amplifier $A_2$ having been preset, any sample S of material under test will provide an output signal to the instrument R that is directly proportional to the degree of absorbance or transmittance of the calibrated sample $S_c$.

As aforementioned, the sensitivity of the photodiode D to light varies with the temperature of said diode. Consequently, it is desirable, for maximum stability of operation for the system, that the temperature of the diode be maintained at a preselected level which, for the present use, has been determined to be 25° C.

Figure 2:
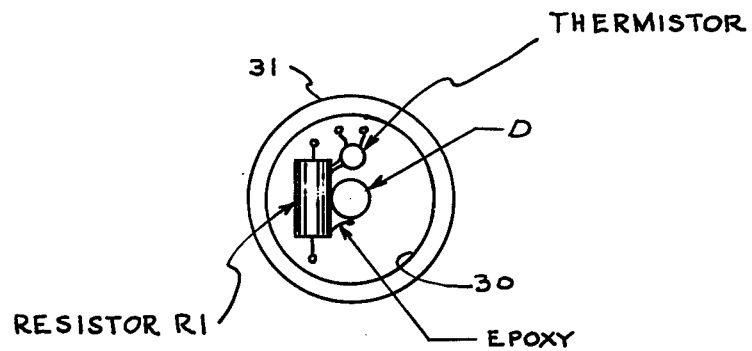
FIG. 2 is a plan view of the photodiode temperature controller.
Figure 3:
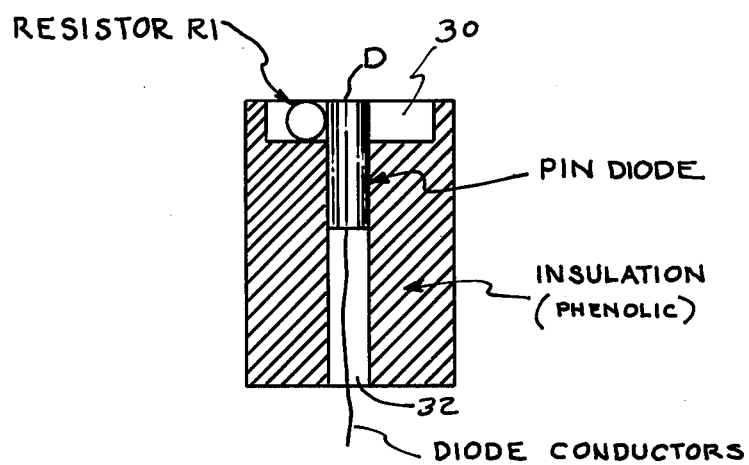
FIG. 3 is a vertical sectional view of the temperature controller for the photodiode taken on approximately the line 3—3 in FIG. 2.

For this purpose, a temperature controller (FIG. 4A) is porovided and with reference to FIGS. 1, 2 and 3, the photodiode D is seen to be centrally mounted within a cavity 30 formed in the upper end of cylindrical housing 31, and extendng partially downwardly into channel 32, the latter enabling the diode conductors to be connected into the system circuitry.

A suitable thermistor $T_1$, preferably one having a negative temperature coefficient (NTC), is disposed within housing cavity 30, as shown particularly in FIG. 2, being in close proximity to the photodiode D and thus positioned to be in heat transfer relation thereto.

A resistor element $R_1$ is also disposed within housing cavity 30. The housing 30 is constructed of a suitable insulative material such as phenolic to thereby assist in retaining the temperature of the photodiode D at the desired level.

As seen in FIG. 4A the thermistor $T_1$ is connected by conductor a to the input circuit of a conventional operational amplifier $A_3$. The output of said amplifier is connected by conductors 35 and b to one end of resistor $R_1$, the opposite end of said resistor being connected to the instrument ground. Said resistor $R_1$ thus provides a load into which the amplifier operates.

With this circuitry for amplifier $A_3$, and with the voltage sources connected thereto as indicated in FIGS. 1 and 4A, current will begin to flow in thermistor $T_1$, the latter initially exhibiting a relatively high resistance. This current flow generates heat which decreases the resistance of the thermistor $T_1$ which, in turn, increases the current flow in amplifier $A_3$ and through its output load resistor element $R_1$. This process is cumulative and continues until the thermistor reaches the desired temperature which is reflected into the surrounding area effective to maintain the photodiode D at the optium temperature level of 25° C, at which time, a stable state will exist. Thereafter, the operational response of the photodiode D to the light from the test sample S and calibration sample $S_c$ will be substantially the same throughout its operative range.

Having thus described a preferred embodiment of photometric measurement system of the present invention, it will be apparent to one skilled in the art that the concepts thereof are susceptible to various modifications and changes without departing from the said concepts are as defined in the appended claims.

What is claimed is:

1. An asborption photometric measurement system comprising, a light source for projecting light onto a liquid sample under test, a photodiode disposed in light interrrupting position with respect to the light passing through said sample, signal amplifier means having a high impedance input and an input bias current less than ten pico amperes, said photodiode having its anode-cathode circuit connected in series circuit relation between the input of said amplifier means and the system ground, said photodiode being operable to provide an open circuit voltage signal across its anode-cathode junction whose magnitude is linearly proportioned to the absorbance of the sample under test, and second circuit means operably connected to the amplifier means and including means adjustable to preset said second circuit means at a preselected operational level whereby said amplifier means is responsive to the output signal of said photodiode to provide a signal that is directly representative of the absorbance of light by said sample under test.

2. In an absorption photometric measurement system as defined in claim 1 and wherein temperature control means are provided to maintain the photodiode at a desired operating tempertaure.

3. In an absorption photometric measurement system as defined in claim 2 and wherein the temperature control means includes a thermistor in heat transfer relation to the photodiode and second amplifier means connected to said thermistor and operable to provide a signal that is responsive to the temperature of said thermistor.

* * * * *